US012270065B2

(12) United States Patent
Royer et al.

(10) Patent No.: US 12,270,065 B2
(45) Date of Patent: Apr. 8, 2025

(54) METHODS FOR IMPROVING TITER AND PURITY OF BETA CAROTENE FERMENTATION IN BLAKESLEA TRISPORA (BETA-CAROTENE FERMENTATION METHOD)

(71) Applicant: DSM IP Assets B.V., Heerlen (NL)

(72) Inventors: John Royer, Kaiseraugst (CH); Emily Davis Streaker, Kaiseraugst (CH); Warren Nelson Itterly, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 510 days.

(21) Appl. No.: 17/631,647

(22) PCT Filed: Aug. 3, 2020

(86) PCT No.: PCT/EP2020/071767
§ 371 (c)(1),
(2) Date: Jan. 31, 2022

(87) PCT Pub. No.: WO2021/019101
PCT Pub. Date: Feb. 4, 2021

(65) Prior Publication Data
US 2022/0290205 A1 Sep. 15, 2022

Related U.S. Application Data

(60) Provisional application No. 62/881,789, filed on Aug. 1, 2019.

(51) Int. Cl.
C12P 23/00 (2006.01)
C12N 1/38 (2006.01)
C12P 5/00 (2006.01)

(52) U.S. Cl.
CPC ............... C12P 23/00 (2013.01); C12N 1/38 (2013.01); C12P 5/007 (2013.01)

(58) Field of Classification Search
None
See application file for complete search history.

(56) References Cited

U.S. PATENT DOCUMENTS

2004/0067550 A1 4/2004 Costa Perez et al.
2007/0166782 A1 7/2007 Keasling et al.

FOREIGN PATENT DOCUMENTS

| CN | 102757995 | 10/2012 |
| CN | 103012230 | 4/2013 |
| CN | 103436584 | 12/2013 |
| CN | 103484520 | 1/2014 |
| CN | 104046674 | 9/2014 |
| CN | 104561211 | 4/2015 |
| CN | 107604036 | 1/2018 |
| CN | 109280685 | 1/2019 |
| EP | 1 367 131 | 12/2003 |
| WO | 97/36996 | 10/1997 |
| WO | WO 02/10429 | 2/2002 |
| WO | WO 2006/102342 | 9/2006 |
| WO | WO 2008/042338 | 4/2008 |
| WO | WO 2014/096992 | 6/2014 |

OTHER PUBLICATIONS

Mazzanti, G. et al. 2016. Curcumin and resveratrol in the management of cognitive disorders: what is the clinical evidence? Molecules 21(1243): 1-27; specif. pp. 2, 3 (Year: 2016).*
Rajput, N. et al. 2013. The effect of dietary supplementation with the natural carotenoids curcumin and lutein on broiler pigmentation and immunity. Poultry Science 92: 1177-1185; specif. p. 1178 (Year: 2013).*
Kim, S.-W. et al. 1997. Enhanced production of beta-carotene from Blakeslea trispora with Span 20. Biotechnology Letters 19(6):561-562; specif. pp. 561, 562 (Year: 1997).*
Choudhari, S.et al. 2008. Media optimization for the production of beta-carotene by Blakeslea trispora: a statistical approach. Bioresource Technology 99: 722-730 specif. pp. 722, 725, 727 (Year: 2008).*
International Search Report for PCT/EP2020/071767 mailed Nov. 4, 2020, 3 pages.
Written Opinion of the ISA for PCT/EP2020/071767 mailed Nov. 4, 2020, 6 pages.
Zhang et al., "Natural fatty acid synthase inhibitors as potent therapeutic agents for cancers: A review", Pharmaceutical Biology, vol. 54, No. 9, 2016, pp. 1919-1925.
Volak et al., "Curcuminoids inhibit multiple human cytochromes P450 (CYP), UDP-glucuronosyltransferase (UGT), and sulfotransferase (SULT) enzymes, while piperine is a relatively selective CYP3A4 inhibitor", NIH Public Access—Drug Metab Dispos, vol. 36(8), Aug. 2008, pp. 1594-1605.
Slayden et al., "Isoniazid affects multiple components of the type II fatty acid synthase system of Mycobacterium tuberculosis", Molecular Biology, vol. 38(3), pp. 514-525, 2000.
Mussagy et al., "Production and extraxtion of carotenoids produced by microorganisms", Applied Microbiology and Biotechnology, vol. 103, 2019, pp. 1095-1114.
Desta, Zeruensenay et al., "Inhibition of Cytochrome P450 (CYP450) Isoforms by Isoniazid: Potent Inhibition of CYP2C19 and CYP3A", Antimicrobial Agents and chemotherapy, vol. 45, No. 2, pp. 382-392, Feb. 2001.

* cited by examiner

Primary Examiner — Adam Weidner
Assistant Examiner — Sharon M. Papciak
(74) Attorney, Agent, or Firm — NIXON & VANDERHYE P.C.

(57) ABSTRACT

The present invention is related to the production of bio-based carotenoids, particularly to methods for enhancing the titer and purity of beta-carotene fermentation in a suitable host cell.

12 Claims, No Drawings

METHODS FOR IMPROVING TITER AND PURITY OF BETA CAROTENE FERMENTATION IN BLAKESLEA TRISPORA (BETA-CAROTENE FERMENTATION METHOD)

This application is the U.S. national phase of International Application No. PCT/EP2020/071767 filed Aug. 3, 2020 which designated the U.S. and claims priority to U.S. Provisional Application No. 62/881,789 filed Aug. 1, 2019, the entire contents of each of which are hereby incorporated by reference.

The present invention is related to the production of bio-based carotenoids, particularly to methods for enhancing the titer and purity of beta-carotene fermentation in a suitable host cell.

For commercial production of carotenoids, such as e.g. lycopene or beta-carotene, both chemical and biotechnological synthesis are competing. In nature, carotenoids are synthesized by certain bacteria, fungi and photosynthetic organisms. Whereas chemically produced beta-carotene is only available in all-trans configuration, naturally produced beta-carotene is available in various configurations, such as all-trans, mono-cis, di-cis and poly-cis. The most commonly used host systems in biotechnological production of beta-carotene with commercial relevance are algae, such as e.g. *Dunaliella salina*, or *Haematococcus pluvialis*, and fungi, such as e.g. *Blakeslea trispora* (for an overview, see e.g. Mussagy et al., Appl Microbiol Biotechnol 103:1095-1114 (2019).

To improve productivity and to suppress the formation of impurities, particularly formation of 7,8-dihydro-beta-carotene, in bio-production of beta-carotene, antibiotics such as e.g. isoniazid have been included in fermentations.

While the mode of action of isoniazid in beta-carotene formation is unknown, isoniazid has been identified in other contexts as an inhibitor of fatty acid synthase (Slayden et al., Mol Microbiol, 38, p. 514-525, 2000) as well as cytochrome P450 enzymes (Desta et al., Antimicrob Agents Chemother, Vol. 45, No 2, p. 382-392, 2001).

The use of antibiotics including isoniazid in large scale is under scrutiny due to a potential role in spread of antibiotic resistance bacteria and therefore should be minimized in biological production processes.

Thus, there is a need to identify new natural compounds which can effectively replace isoniazid in the carotenoid production via fermentation of suitable carotenoid-producing host cells, such as e.g. *Blakeslea trispora*.

Surprisingly, we now found that the presence of curcumin in beta-carotene fermentations of suitable carotenoid-producing host cells, such as e.g. *Blakeslea trispora*, has a stimulatory effect on beta-carotene formation and simultaneously is capable of reducing impurities, such as in particularly reducing the percentage of 7,8-dihydro-beta-carotene.

Particularly, the present invention is related to a process for fermentative production of carotenoids in a carotenoid-producing host cell as defined herein, such as e.g. in *B. trispora* as host system, wherein the fermentation is performed in the presence of an effective amount of curcumin, such as via addition of curcumin during the fermentation, preferably at curcumin concentrations below about 1.0% (w/v).

In one aspect, the present invention is directed to a process for production of carotenoids in a carotenoid-producing host cell, such as e.g. *B. trispora*, in the presence of an effective amount of curcumin added during the fermentation, particularly wherein the production of beta-carotene is increased by at least about 12% compared to fermentation without addition of curcumin. Preferably, an increase in beta-carotene of more than about 220% could be achieved, such as e.g. in the presence of about 0.3% curcumin during the fermentation.

Particularly, the process according to the present invention for fermentative production of carotenoids in a carotenoid-producing host cell, such as e.g. *B. trispora* as host system, is conducted in the presence of about 0.01 to 1.0% (w/v) curcumin during the fermentation, preferably about 0.03 to 1.0% (w/v), such as e.g. in the range of about 0.03 to 0.05 curcumin which might be particularly useful in a (medium/large-scale) fermentor, such as e.g. in the presence of about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1.0%, wherein the amount of produced beta-carotene (g/l) could be increased by a range of about 12 to more than 220% compared to fermentation in the absence of curcumin. More preferably, the fermentation is conducted is in the presence of about 0.3 to 1.0% curcumin (w/v).

In a further aspect, the present invention is related to a process for production of carotenoids in a carotenoid-producing host cell, such as e.g. *B. trispora* as host system, wherein the formation of impurities such as e.g. 7,8-dihydro-beta-carotene generated during the fermentation is reduced, particularly wherein the percentage of 7,8-dihydro-beta-carotene based on total carotenoids generated during the fermentation is in the range of about 7% or less based on total carotenoids, such as a reduction by at least about 28% compared to fermentation without addition of curcumin. A reduction of 7,8-dihydro-beta-carotene based on total carotenoids of about nearly 70% can be achieved, such as e.g. reduction of about 68%, i.e. about 70% less 7,8-dihydro-beta-carotene based on total carotenoids formed during the fermentation, particularly obtainable via addition of about 1.0% (w/v) curcumin during the fermentation.

Preferably, the process according to the present invention for fermentative production of carotenoids in a carotenoid-producing host cell, such as e.g. *B. trispora* as host system, is conducted in the presence of about 0.01 to 1.0% (w/v) curcumin, preferably about 0.03 to 1.0% (w/v), such as e.g. in the presence of about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1.0%, wherein the percentage of 7,8-dihydro-beta-carotene based on total carotenoids could be reduced from about 9.7% (without curcumin) to a range of about 7 to 3% (in the presence of curcumin). More preferably, is a process in the presence of about 0.3 to 1.0% curcumin, leading to maximal reduction of 7,8-dihydro-beta-carotene, i.e. levels of about 3% 7,8-dihydro-beta-carotene based on total carotenoids.

Thus, the present invention is directed to a method for reduction of impurities in carotenoid-production in a carotenoid-producing host cell, such as e.g. *B. trispora* as host system, particularly reduction of 7,8-dihydro-beta-carotene impurities in fermentation process of producing beta-carotene, said method comprising the addition of an effective amount of curcumin during the fermentation, particularly the presence of about 1.0% or less curcumin (w/v) during the fermentation, more particularly an amount of about 0.3 to 1.0% curcumin (w/v) added during the fermentation.

In another embodiment, the present invention is directed to a method for increasing the percentage of beta-carotene in carotenoid-production in a carotenoid-producing host cell, such as e.g. *B. trispora* as host system, comprising addition of an effective amount of curcumin during the fermentation, particularly fermentations in the presence of about 1.0% or less curcumin, wherein the percentage of beta-carotene based on total carotenoids can be increased by about 3 to 11% compared to fermentations without curcumin.

In one aspect of the present invention, a process for production of carotenoids in a carotenoid-producing host cell, such as e.g. *B. trispora* as host system, is provided, wherein the percentage of beta-carotene based on total carotenoids could be increased, particularly wherein the percentage of beta-carotene based on total carotenoids is increased to more than about 90%, such as e.g. 92%, compared to fermentations without the presence of curcumin during the fermentation, preferably wherein the percentage of beta-carotene is in the range of about 86 to 92%, such as e.g. in the presence of 1.0% curcumin added during the fermentation, compared to a percentage of about 83% without addition of curcumin during the fermentation.

A further preferred embodiment is a fermentation process in the presence of 0.3% curcumin, leading to percentage of about 91% beta-carotene based on total carotenoids, i.e. an increase by about 10% compared to fermentations without curcumin. This effect is even higher than fermentations in the presence of 0.28 g/l isoniazid leading to an increase of less than 10% as compared to fermentations without addition of isoniazid.

In a particular embodiment, the carotenoid-production in a carotenoid-producing host cell, such as e.g. *B. trispora*, as described herein is conducted without addition of antibiotics, particularly without addition of isoniazid, during the fermentation.

As used herein, the term "1.0% (w/v)" means 1% by weight of the fermentation medium.

The term "an effective amount of curcumin" in connection with the present invention means a concentration of at least about 0.01%, such as e.g. a range of about 0.01 to 1% and more, preferably about 0.01, 0.02, 0.03, 0.04, 0.05, 0.06, 0.07, 0.08, 0.09, 0.1, 0.2. 0.25, 0.3, 0.35, 0.4, 0.45, 0.5, 0.55, 0.6, 0.65, 0.7, 0.75, 0.8, 0.85, 0.9, 0.95, 1.0 or more. Particularly, effective amount of curcumin with regards to shake flask experiments might be concentration in the range of about 0.1 to 1.0%. Particularly, effective amount of curcumin with regards to (middle/large-scale) fermentors might be concentrations in the range of about 0.01 to 0.05%.

Curcumin to be used in an effective amount as defined herein might be originated from *Curcuma longa* (turmeric) root in the form of ground turmeric comprising curcuminoids, with curcumin being the principal curcuminoid of turmeric. It includes but is not limited to curcumin or derivatives thereof such as e.g. demethoxycurcumin and bisdemethoxycurcumin. Curcumin may be purified from turmeric to 95%, may be present at 37-55% in oleoresin turmeric, 6-15% in diluted oleoresins or in other forms as available under CAS No. 458-37-7 from various commercial suppliers.

As used herein, the term "impurities" includes but is not limited to 7,8-dihydro-beta-carotene, gamma-carotene and cis beta-carotene, particularly 7,8-dihydro-beta-carotene.

Suitable host cells to be used for a process according to the present invention include microorganisms capable of carotenoid biosynthesis selected from bacteria, algae or fungi, particularly yeast, such as e.g. selected from *Escherichia, Streptomyces, Pantoea (Erwinia), Bacillus, Flavobacterium, Synechococcus, Lactobacillus, Corynebacterium, Micrococcus, Mixococcus, Brevibacterium, Bradyrhizobium, Gordonia, Dietzia, Muricauda, Sphingomonas, Synochocystis, Paracoccus, Saccharomyces, Aspergillus, Pichia, Hansenula, Yarrowia, Phycomyces, Mucor, Rhodotorula, Sporobolomyces, Xanthophyllomyces, Phaffia, Blakeslea, Haematococcus, Chlorella, Dunaliella, Neospongicoccum, Chlaydomonas, Murielopsus*, or *Scenedesmus*, e.g. selected from *Escherichia coli, Paracoccus xeaxanthinifaciens, Saccharomyces cerevisiae, Aspergillus niger, Pichia pastoris, Hansenula polymorpha, Phycomyces blakesleanus, Blakeslea trispora, Yarrowia lipolytica* or *Dunaliella salina*. Preferably, the host cell is selected from native carotenoid producers, including *Dunaliella salina, Haematococcus pluvialis, Rhodosporidium, Rhodotorula, Sporobolomyces, Sprodidiobolus, Paracoccus, Fusarium sporotrichioides, Phycomyces blakesleanus, Mucor circinellioides, Blakeslea*, more preferably from *B. trispora*.

With regards to the present invention, it is understood that organisms, such as e.g. microorganisms, fungi, algae or plants also include synonyms or basonyms of such species having the same physiological properties, as defined by the International Code of Nomenclature of Prokaryotes or the International Code of Nomenclature for algae, fungi, and plants (Melbourne Code).

The term "carotenoids" as used herein is well known in the art. It includes long, 40 carbon conjugated isoprenoid polyenes that are formed in nature by the ligation of two 20 carbon geranylgeranyl pyrophosphate molecules. These include but are not limited to phytoene, lycopene, and carotene, such as e.g. beta-carotene, which can be oxidized on the 4-keto position or 3-hydroxy position to yield canthaxanthin, zeaxanthin, or astaxanthin. Cultivation and isolation of beta-carotene-producing host cells selected from *Yarrowia* and *Saccharomyces* is described in e.g. WO2008042338 or WO2014096992. Biosynthesis of carotenoids using fungal host is described in e.g. WO2006102342. With regards to production of beta-carotene in *E. coli* as host cell, methods are described in e.g. US20070166782. Carotenoid production in *Blakeslea trispora* is described in e.g. EP1367131 or WO2002010429.

The bio-based carotenoids, particularly beta-carotene, as described herein can be used as ingredients, such as e.g. in the form of crystals, in the food, feed, cosmetic or pharma industry known to the skilled person.

Particularly, the present invention features the following embodiments:

(1) A method for enhancing the titer of beta-carotene production in a fermentation process of producing beta-carotene in *Blaskeslea trispora*, wherein the method comprises adding an effective amount of curcumin during the fermentation.

(2) The method as of embodiment (1), wherein said curcumin is added in the amount of 1.0% or less by weight of the fermentation medium.

(3) The method as of embodiments (1) or (2), wherein said curcumin is added in the amount of 0.3% or less by weight of the fermentation medium.

(4) The method as of embodiments (1), (2), or (3), wherein said curcumin is added in the amount of 0.1% or less by weight of the fermentation medium.

(5) The method as of embodiments (1), (2), (3), or (4), wherein said curcumin is added in the amount of 0.03% or less by weight of the fermentation medium.

(6) The method of as of embodiments (1), (2), (3), (4), or (5), wherein said method further reduces the amount of 7,8-dihydro-beta-carotene produced during the fermentation.

(7) The method as of embodiments (1), (2), (3), (4), (5) or (6), wherein the amount of 7,8-dihydro-beta-carotene generated during the fermentation is less than 7% by weight of the fermentation medium.

(8) The method as of embodiments (1), (2), (3), (4), (5), (6) or (7), wherein isoniazid is not added during the fermentation.

(9) A method for reducing the amount of 7,8-dihydro-beta-carotene generated in a fermentation process of producing beta-carotene in *Blaskeslea trispora*, wherein the method comprises adding an effective amount of curcumin during the fermentation.

(10) The method as of embodiment (9), wherein said curcumin is added in the amount of 1.0% or less by weight of the fermentation medium.

(11) The method as of embodiments (9) or (10), wherein said curcumin is added in the amount of 0.3% or less by weight of the fermentation medium.

The following examples are illustrative only and are not intended to limit the scope of the invention in any way. The contents of all references, patent applications, patents and published patent applications, cited throughout this application are hereby incorporated by reference, in particular WO2008042338, WO2014096992, WO2006102342, US20070166782, EP1367131, WO2002010429.

EXAMPLES

Example 1: General Methods, Strains and Plasmids

Shake flask seed medium MIBLT-1. 23.5 g/l corn meal, 23 g/l soybean meal, 10 g/l glucose, 0.5 g/l $KH_2PO_4$ are mixed, the medium pH is adjusted to 6.3, homogenized with an Ultra-Turrax® blender (Ika) for 8 minutes at 13500 rpm, and heated at 70° C. for 45 minutes prior to autoclaving.

Shake flask production medium MF-BLT-22. 17.5 g/l corn meal, 40 g/l soya flour, 10 g/l soy lecithin, 0.5 g/l $KH_2PO_4$, 109 g/l soy oil, optionally 0.28 g/l isoniazid, optionally curcumin (1.0, 0.3, 0.1, 0.03 or 0.01% w/v), are mixed, the medium pH is adjusted to 6.3, is homogenized with an Ultra-Turrax® blender (Ika) for 8 minutes at 13500 rpm, and heated at 70° C. for 45 minutes prior to autoclaving.

Solution A. Dichloromethane and methanol are mixed in 1:1 ratio.

Shake Flask Process. An Erlenmeyer flask (250 or 300 mL volume) containing 30 ml of seed medium (MIBLT-1) is inoculated with spores of *B. trispora* (−) strain to a concentration of $4.5 \times 10^3$ spores/ml. A second Erlenmeyer flask containing 30 ml of MIBLT-1 is inoculated with spores of *B. trispora* (+) strain to a concentration of $1.5 \times 10^3$ spores/ml. The flasks are incubated (220 rpm, 5 cm displacement, 27° C., protected from light) for 48 hr. Three ml of (+) strain culture are added to 30 ml of (−) strain culture, and the mated strains mixture is incubated (220 rpm, 5 cm throw, 27° C., protected from light) for 45 minutes. Erlenmeyer flasks (250 or 300 mL volume) containing 20 ml of production medium (MF-BLT-22) are inoculated with 2 ml of the mated strains mixture. Flasks are incubated (250 rpm, 5 cm displacement, 25° C., protected from light). At 48 hours after inoculation of the 20 mL production cultures, 40 μL of a 50% v/v sterile beta-ionone solution in absolute ethanol is added to each flask. Cultures are returned to the incubator for a total of 7 days post inoculation.

Sample preparation for HPLC-analysis. Each flask culture is transferred to a 50 mL conical tube and homogenized with an Ultra-Turrax® blender (Ika) for 2 minutes at 24000 rpm. Weigh out one gram of sample into a 100 ml volumetric flask. Eighty milliliters of Solution A are added to the flask and the flask is sonicated for 5 min. The volume is brought to 100 ml with solution A, and the solution is stirred for 60 minutes and allowed to settle for another hour.

HPLC-analysis. Samples from the above extract (10 μl) are injected as is on a calibrated HPLC using a Suplex-PKB-100 column (Supelco), with a flow rate of 0.6 ml/min, and column temperature of 30° C. The mobile phase contains (per L) 455 ml acetonitrile, 500 ml methanol, 0.2 ml N-ethyldiisopropylamine, 25 ml aqueous solution of 0.2% ammonium acetate, and 50 mg BHT (dissolved in 20 ml of 2-propanol). Compounds are identified and quantified by UV at 448 nm.

Example 2: Effect on Beta-Carotene Production with *B. trispora* in the Presence of Curcumin Concentration of beta-carotene was measured as described in Example 1, with comparison of different concentrations of curcumin. As shown in Table 1, the highest increase in beta-carotene was observed with 0.3% (w/v) curcumin added to the production medium. Addition of 0.28 g/l isoniazid resulted in 4.17 g beta-carotene per l, thus less than with the addition of 0.3% or 1.0% curcumin.

TABLE 1

Effect of curcumin on formation of beta-carotene ("BC"). "Increase BC" means the increased percentage in the presence of curcumin compared to beta-carotene production in the control ("None") with no curcumin/isoniazid present in the medium (average of two measurements). For more details, see text.

| Curcumin [w/v] | Isoniazid [g/l] | BC [g/L] | Increase BC |
| --- | --- | --- | --- |
| None | None | 1.55 | n.a. |
| None | 0.28 | 4.17 | n.a. |
| 0.01% | None | 1.74 | 12% |
| 0.03% | None | 2.45 | 58% |
| 0.1% | None | 3.48 | 125% |
| 0.3% | None | 4.99 | 222% |
| 1.0% | None | 4.55 | 194% |

Example 3: Effect on Beta-Carotene Purity Profile with *B. trispora* in the Presence of Curcumin Fermentations and analysis were performed as described in Ex. 2, including addition of various concentrations of curcumin. The formation of beta-carotene and 7,8-dihydro-beta-carotene was analyzed by HPLC (see Ex. 1) and as shown in Table 2. Best results were obtained in the presence of 0.3 to 1.0% (w/v) curcumin, with an increase in the percentage of beta-carotene based on total carotenoids of 10.3 to 11.2% and a reduction in the percentage of 7,8-dihydro-beta-carotene based on total carotenoids of 65.4 to 67.7%. Addition of isoniazid resulted in a carotenoid-mix with a percentage of 28.1% 7,8-dihydro-beta-carotene and an increase of less than 10% in the percentage of beta-carotene (both based on total carotenoids).

TABLE 2

Effect of curcumin on formation of beta-carotene ("BC"), 7,8-dihydro-beta-carotene ("7,8-DH") shown as percentage of total carotenoids. "None" means no curcumin was present in the medium (average of two measurements). For more details, see text.

| Curcumin [w/v] | BC [%] | 7,8-DH [%] |
| --- | --- | --- |
| None | 82.87 | 9.67 |
| 0.01% | 81.19 | 9.98 |
| 0.03% | 85.59 | 6.99 |

TABLE 2-continued

Effect of curcumin on formation of beta-carotene ("BC"),
7,8-dihydro-beta-carotene ("7,8-DH") shown as percentage
of total carotenoids. "None" means no curcumin was present
in the medium (average of two measurements). For more details, see text.

| Curcumin [w/v] | BC [%] | 7,8-DH [%] |
|---|---|---|
| 0.1% | 86.75 | 5.79 |
| 0.3% | 91.44 | 3.35 |
| 1.0% | 92.17 | 3.12 |

The invention claimed is:

1. A process for fermentative production of beta-carotene, the process comprising:
   (a) conducting fermentation production of beta-carotene with *Blakeslea trispora* as a carotenoid-producing host cell, and
   (b) adding during the fermentation of step (a) an amount of 0.01 to 1.0% (w/v) of curcumin effective to increase the beta-carotene during fermentation by at least 12% as compared to fermentation without addition of curcumin.

2. The process according to claim 1, wherein step (b) comprises adding the curcumin during fermentation according to step (a) in an amount of 0.3 to 1.0% (w/v).

3. The process according to claim 1, wherein 7,8-dihydro-beta-carotene is formed during the process, and wherein the formation of 7,8-dihydro-beta-carotene during the fermentation of step (a) is reduced by the addition of the curcumin according to step (b).

4. The process according to claim 3, wherein the formation of 7,8-dihydro-beta-carotene is reduced to 7% or less, based on total carotenoids formed during the fermentation.

5. The process according to claim 3, wherein the percentage of 7,8-dihydro-beta-carotene formed during the fermentation is reduced by substantially 70% as compared to conducting the fermentation of step (a) without addition of curcumin according to step (b).

6. The process according to claim 3, wherein the formation of 7,8-dihydro-beta-carotene is reduced to about 3% or less, based on total carotenoids formed during the fermentation.

7. The process according to claim 1, wherein the production of beta-carotene during the fermentation according to step (a) is increased by about 3 to 11%, based on total carotenoids formed during the fermentation, as compared to conducting the fermentation of step (a) without addition of curcumin according to step (b).

8. The process according to claim 7, wherein the production of beta-carotene during fermentation according to step (a) is 90% or more, based on total carotenoids formed during the fermentation, as compared to conducting the fermentation of step (a) without addition of curcumin according to step (b).

9. The process according to claim 1, wherein the fermentation according to step (a) is performed in the absence of isoniazid.

10. A method to reduce formation of 7,8-dihydro-beta-carotene during a beta-carotene fermentative production process comprising:
    (a) conducting fermentation production of beta-carotene with *Blakeslea trispora* as a carotenoid-producing host cell, and
    (b) adding curcumin during the fermentation of step (a) in an effective amount of 0.01 to 1.0% (w/v) to reduce formation of 7,8-dihydro-beta-carotene during fermentation to 7% or less, based on total carotenoids formed during the fermentation, as compared to fermentation without addition of curcumin.

11. The method according to claim 10, wherein the formation of 7,8-dihydro-beta-carotene is reduced to 3% or less, based on total carotenoids formed during the fermentation, as compared to fermentation without addition of curcumin.

12. The method according to claim 10, wherein the effective amount of curcumin is 0.3 to 1.0% (w/v).

* * * * *